(12) United States Patent
Hong et al.

(10) Patent No.: US 8,685,440 B2
(45) Date of Patent: Apr. 1, 2014

(54) NANOLIPOSOME USING ESTERIFIED LECITHIN AND METHOD FOR PREPARING THE SAME, AND COMPOSITION FOR PREVENTING OR TREATING SKIN DISEASES COMPRISING THE SAME

(75) Inventors: Joon Pio Hong, Seoul (KR); Sang Kil Lee, Gyeonggi-do (KR); Won Chul Kim, Gyeonggi-do (KR); Chae Ha Yoon, Gyeonggi-do (KR); Sang Wook Lee, Seoul (KR); Kyeong Sun Shin, Gyeonggi-do (KR); Seung Kook Park, Seoul (KR)

(73) Assignee: Daewoong Co., Ltd, Kyunggi-Do (KR)

( * ) Notice: Subject to any disclaimer, the term of this patent is extended or adjusted under 35 U.S.C. 154(b) by 570 days.

(21) Appl. No.: 12/375,739

(22) PCT Filed: Aug. 1, 2007

(86) PCT No.: PCT/KR2007/003699
§ 371 (c)(1),
(2), (4) Date: Mar. 31, 2009

(87) PCT Pub. No.: WO2008/016258
PCT Pub. Date: Feb. 7, 2008

(65) Prior Publication Data
US 2009/0263473 A1    Oct. 22, 2009

(30) Foreign Application Priority Data
Aug. 2, 2006  (KR) .................... 10-2006-0072809

(51) Int. Cl.
*A61K 36/00*    (2006.01)
*A61K 9/127*    (2006.01)
*A61K 8/14*     (2006.01)
*A61K 8/55*     (2006.01)

(52) U.S. Cl.
CPC .............. *A61K 9/1271* (2013.01); *A61K 8/14* (2013.01); *A61K 8/553* (2013.01); *A61K 9/1277* (2013.01)
USPC ........................ 424/450; 424/94.1; 424/725

(58) Field of Classification Search
None
See application file for complete search history.

(56) References Cited

U.S. PATENT DOCUMENTS

| | | | |
|---|---|---|---|
| 4,944,948 A | * | 7/1990 | Uster et al. ............... 424/450 |
| 5,310,958 A | | 5/1994 | Mizushima |
| 5,498,420 A | * | 3/1996 | Mentrup Edgar et al. ..... 424/450 |
| 5,679,374 A | * | 10/1997 | Fanchon et al. ............ 424/450 |
| 5,998,480 A | * | 12/1999 | Giorgetti .................. 514/604 |

FOREIGN PATENT DOCUMENTS

| | | |
|---|---|---|
| JP | 03048614 | 3/1991 |
| KR | 10-2005-0058635 | 6/2005 |
| KR | 10-2006-0025423 | 3/2006 |
| KR | 100768151 | 10/2007 |
| WO | WO 90/11781 | 10/1990 |
| WO | WO 01/62276 A1 | 8/2001 |
| WO | WO 2004/100998 A2 | 11/2004 |
| WO | WO 2004/100998 A3 | 11/2004 |
| WO | WO 2005/049080 A1 | 6/2005 |

OTHER PUBLICATIONS

Lecithin Guide.Info (2008) http://www.lecithinguide.info/index.html.*

* cited by examiner

*Primary Examiner* — Janet Epps-Smith
(74) *Attorney, Agent, or Firm* — Swanson & Bratschun, L.L.C.

(57) ABSTRACT

The present invention relates to a nanoliposome comprising a liposome membrane containing esterified lecithin, and one or more physiologically active ingredients included in inner space of the liposome membrane; a method for preparing the same; and a composition for preventing or treating skin diseases, comprising the same. The nanoliposome according to the present invention has long-term stability and uniformity, and so can be used to prepare a composition for skin having excellent moisturizing and penetrating properties, such as cosmetics, medicament for treating skin diseases, or the like. In particular, the present composition for preventing or treating skin diseases comprises epidermal growth factor included in the nanoliposome, thereby showing an excellent effect of stimulating skin-penetration and good pharmaceutical stability. Also, the esterified lecithin used in preparing liposome can provide effects of softening skin and stimulating skin-penetration, thereby enhancing the penetration of epidermal growth factor and natural extract into skin, as well as additional moisturizing effect which is advantageous in treating skin diseases. Further, since the present composition comprises nanoliposome prepared by containing esterified lecithin in liposome membrane, the conventional problems of heating and dispersing active ingredients at high temperature (70° C. or more), low stability and uniformity, or the like can be solved.

13 Claims, 2 Drawing Sheets

NANOLIPOSOME USING ESTERIFIED LECITHIN AND METHOD FOR PREPARING THE SAME, AND COMPOSITION FOR PREVENTING OR TREATING SKIN DISEASES COMPRISING THE SAME

RELATED APPLICATIONS

This application is a 35 U.S.C. § 371 national phase application of PCT/KR2007/003699 (WO 2008/016258), filed on Aug. 1, 2007, entitled "Nanoliposome Using Esterified Lecithin and Method for Preparing the Same, and Composition for Preventing or Treating Skin Diseases Comprising the Same," which application claims the benefit of Korean Patent Application Serial No. 10-2006-0072809, filed on Aug. 2, 2006. Each of these applications is specifically incorporated herein by reference in its entirety.

TECHNICAL FIELD

The present invention relates to a nanoliposome comprising a liposome membrane containing esterified lecithin, and one or more physiologically active ingredients included in inner space of the liposome membrane; a method for preparing the same; and a composition for preventing or treating skin diseases comprising the same.

BACKGROUND ART

Liposome is a micro endoplasmic reticulum having a closed double-layered lipid membrane, in which a hydrophilic space exists. Accordingly, liposome is characterized in containing water-soluble materials in the hydrophilic inner space and capturing oil-soluble materials in the outer double-layered lipid membrane. A material which forms such liposome membrane is called as lipoid. As the lipoid, phosphoglycerides or sphingolipids are conventionally used. Lecithin or ceramide is most generally used in the field of cosmetics or foods since they have excellent moisturizing property and no toxicity to human body.

However, these lecithin and ceramide are hydrophobic, and so hard to disperse in alcohol solution as well as aqueous solution. Thus, to be used as lipoid, they have to be dispersed with heating to a high temperature of 70° C. or more, and then functional materials have to be added thereto. Accordingly, there is a very big problem in liposomizing functional compounds which are oxidized at high temperature or are thermally unstable, such as coenzyme Q10 and EGF. Also, thus formed liposome has disadvantages of very low stability and non-uniformity in the size. In particular, it is difficult to liposomize two functional compounds which have very different polarity from each other, such as hydrophobic coenzyme Q10 and hydrophilic EGF, together.

Recently, anionic surfactant type of phospholipidyl lipoid obtained by reacting lecithin with phosphoric acid or other polar compounds, thereby having good dispersibility to aqueous solution, is widely used. However, if the lipoid is too hydrophilic, the wettability may be enhanced, but the penetration effect into skin is greatly diminished due to the difference in polarity with ingredients on skin surface. Also, if the lipoid is anionic salt type, it decreases the viscosity of cosmetics, thereby requiring further addition of thickening agents.

Originally, coenzyme Q10 is known as a co-enzyme promoting energy generation of cell in human body, having potent anti-oxidation power against active oxygen. Thus, its intake or application to skin can prevent the oxidation of cells, thereby maintaining skin elasticity and preventing the aging effectively. In particular, in human body, such coenzyme Q10 is produced in a sufficient amount up to 20 years old, but the amount decreases from the peak before or after 20 years old due to various reasons such as unbalanced diet, stress, or the like. Before or after 40 years old, the decrease is accelerated, and so supplement thereof is required.

Epidermal Growth Factor (EGF) is a protein which exists in colostrums of mother's milk, and has excellent effects in reproducing cells and promoting the recovery of wound, and so EGF is used as biological medicament for treating foot ulcer of a diabetic. Also, EGF is known as an ingredient having a function of healing a wound naturally without a scar, and known to have skin reproducing effect. Accordingly, it is widely used as a raw material for functional cosmetics, as well as a medicament for healing a wound by diabetic foot ulcer, burn, cut or the like.

Korean Patent Laid-open Publication No. 10-2005-0058635 discloses an extract from Camellia japonica having anti-inflammatory and anti-oxidation activity. Korean Patent Laid-open Publication No. 10-2006-0025423 discloses an extract from *Viscum album* L. var. *coloratum* having anti-inflammatory and anti-oxidation activity.

DISCLOSURE OF THE INVENTION

One object of the present invention is to provide a nanoliposome comprising a liposome membrane containing esterified lecithin, and one or more physiologically active ingredients included in inner space of the liposome membrane. According to the present invention, if a double-layered lipid membrane is formed by using the esterified lecithin which is dispersed well in water or alcohol and has both hydrophilicity and hydrophobicity, a solution of nanoliposome containing functional materials such as coenzyme Q10 or epidermal growth factor can be prepared at low temperature, and such prepared nanoliposome has long-term stability and homogeneity, and so can be used as a raw material for composition for skin having excellent moisturizing and penetrating properties, such as cosmetics, medicament for treating skin diseases, or the like.

Another object of the present invention is to provide a method for preparing a stable nanoliposome by dispersing a mixture solution of esterified lecithin and physiologically active ingredient, in nanometer size.

The present inventors have found that if epidermal growth factor is prepared as nanoliposome and formulated with natural extract having anti-inflammatory activity, the stability is enhanced, and penetration of EGF into skin are promoted, whereby a composition having excellent healing effect to skin diseases can be obtained.

Therefore, another object of the present invention is to provide a composition for preventing or treating skin diseases, comprising nanoliposome in which epidermal growth factor is included, and one or more natural extracts having anti-inflammatory activity.

DETAILED DESCRIPTION OF THE INVENTION

Figure 1:
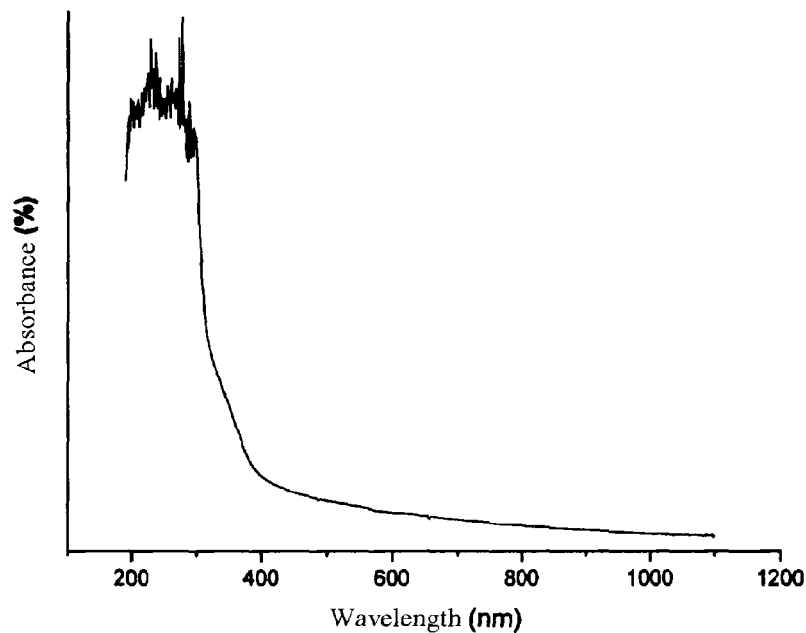
FIG. 1 is a graph representing UV/Visible absorbance (%) of the solution of nanoliposome having double layered membrane of EGF/coenzyme Q10, which is prepared by using esterified lecithin according to the present invention.

One aspect of the present invention provides a nanoliposome comprising a liposome membrane containing esterified lecithin, and one or more physiologically active ingredients included in inner space of the liposome membrane.

Another aspect of the present invention provides a method for preparing a nanoliposome comprising: the $1^{st}$ step of preparing esterified lecithin by reacting lecithin with organic acid; the $2^{nd}$ step of dissolving the esterified lecithin and one or more physiologically active ingredients in a solvent; and the $3^{rd}$ step of dispersing the resultant solution to obtain liposome in nanometer size.

Another aspect of the present invention provides a composition for preventing or treating skin diseases, comprising nanoliposome which comprises a liposome membrane containing esterified lecithin, and epidermal growth factor included in inner space of the liposome membrane; and one or more natural extracts having anti-inflammatory activity.

The present invention is explained in detail below.

The term "inclusion (included or including)" as used herein, refers to contain (contained or containing) of water-soluble material (e.g., epidermal growth factor, ascorbic acid, etc.) in the hydrophilic space in center of the liposome, or capture (captured or capturing) of oil-soluble material (e.g., coenzyme Q10, retinol, retinyl palmitate, ascorbyl palmitate, etc.) by double-layered lipid membrane of the liposome.

The term "nanoliposome" as used herein, refers to a liposome with a diameter of about 100 to 200 nm, conventionally prepared by dispersing liposome in micrometer size under pressure condition of about 1000 psi or more.

In the present invention, the membrane of liposome comprises esterified lecithin. The membrane of liposome may comprise liposome membrane components (i.e. lipoid) which is used conventionally in liposome preparation, if necessary. The lipoid comprises phosphoglycerides or sphingolipids, for example, phosphatidylcholine (i.e., lecithin), hydrogenated lecithin, phosphatidylethanolamine, phosphatidylinositol, ceramide, cerebrosides (i.e., galactosyl ceramide), sphingomyelin, gangliosides, or the like. As the esterified lecithin, the lipoid also can give moisturizing effect. Among the lipoids listed above, hydrogenated lecithin and/or ceramide can be preferably used. The hydrogenated lecithin refers to a lecithin consisting of saturated hydrocarbon which is obtained by the reduction of all unsaturated hydrocarbon in lecithin.

The esterified lecithin contained in the membrane of liposome is dispersed well in water or alcohol, and has both hydrophilicity and hydrophobicity. Accordingly, the esterified lecithin has polarity enough to be dispersed in aqueous solvent, but not enough to be dissolved completely in the aqueous solvent. Thus, when the membrane of liposome is formed by using the esterified lecithin, a stable liposome solution can be prepared even at low temperature such as 20° C. to 60° C.

The esterified lecithin can be prepared by reacting lecithin or hydrogenated lecithin with an organic acid. The esterification process is a condensation reaction wherein the alcoholic group of the lecithin reacts with organic acid, and the resultant water molecule is eliminated therefrom. Thus prepared esterified lecithin reacts with water in aqueous solution, and is dissociated again into lecithin (alcoholic group) and a form of organic acid. Therefore, in this reaction, the esterified lecithin, lecithin (or hydrogenated lecithin) and organic acid coexist, with maintaining proper equilibrium between esterification and dissociation according to acidity, as follows:

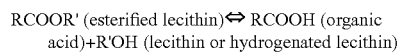

RCOOR' (esterified lecithin)⇔ RCOOH (organic acid)+R'OH (lecithin or hydrogenated lecithin)

The organic acid used in the preparation of the esterified lecithin comprises organic acids conventionally used in cosmetics and foods such as acetic acid, malic acid, lactic acid, glycolic acid, citric acid or oxalic acid, preferably anhydrous organic acids, and more preferably anhydrous malic acid or anhydrous acetic acid. If anhydrous acetic acid is used, the esterified lecithin shows greater hydrophilicity than the case of using anhydrous malic acid. Thus, the organic acid can be selected appropriately, depending on the relative amounts of hydrophilic or hydrophobic functional material to be added, or the degree of polarity of functional material. These organic acids also may exhibit an effect of removing keratinous substance or an effect of skin-softening, if applied to skin.

The esterified lecithin can be used in an amount enough to form liposome, without special limitation, preferably in 1 to 5 parts by weight, based on 1 part by weight of physiologically active ingredient.

The physiologically active ingredient included in inner space of the liposome membrane of the present invention may be, but not limited to, water-soluble drug, oil-soluble drug, thermally unstable functional material or the like. Preferably, the physiologically active ingredient is one or more selected from the group consisting of coenzyme Q10 and epidermal growth factor.

The nanoliposome of the present invention may further comprise one or more selected from the group consisting of triglyceride type organic compound, preferably caprylic/capric triglyceride; anionic surfactant, preferably diethylamine cetylphosphate, ascorbyl phosphate sodium, phosphotidylcholine or triethylamine coconyl glutamine sodium; hydrogenated saturated hydrocarbon lecithin; softening agent, preferably butylated hydroxy toluene, betaine type amphiphilic surfactant preferably such as laurylamine propyl betaine, laurylbetaine, laurylaminebetaine or cocamido propylbetaine; and chelating agent, preferably sodium salt of ethylenediaminetetraacetate.

The present invention also relates to a method for preparing a nanoliposome comprising: the $1^{st}$ step of preparing esterified lecithin by reacting lecithin with organic acid; the $2^{nd}$ step of dissolving the esterified lecithin, and one or more physiologically active ingredients in a solvent; and the $3^{rd}$ step of dispersing the resultant solution to obtain liposome in nanometer size.

In the $1^{st}$ step, the esterified lecithin is prepared by condensation-reaction of lecithin with an organic acid. The organic acid is preferably selected from the group consisting of acetic acid, malic acid, lactic acid, glycolic acid, citric acid and oxalic acid, and anhydrides thereof.

In the $2^{nd}$ step, the physiologically active ingredient is preferably, but not limited to, water-soluble drug, oil-soluble drug, or thermally unstable functional material. More preferably, the physiologically active ingredient is one or more selected from the group consisting of coenzyme Q10 and epidermal growth factor. Also, if required, as physiologically active ingredient, anti-oxidant such as coenzyme Q10, retinol, retinal, retinyl palmitate, retinoic acid, ascorbic acid, ascorbyl phosphate or salts thereof, or ascorbyl palmitate may be further used.

When a hydrophobic ingredient such as coenzyme Q10 and a hydrophilic ingredient such as EGF are used at the same time, the $2^{nd}$ step preferably comprises the steps of: preparing oil-phase solution by dissolving esterified lecithin and hydrophobic active ingredient such as coenzyme Q10 in organic solvent; preparing aqueous phase solution by dissolving hydrophilic active ingredient such as EGF in aqueous solvent; and mixing the oil-phase solution and the aqueous phase solution.

In the above step of preparing oil-phase solution, the esterified lecithin and hydrophobic active ingredient such as coenzyme Q10 are dissolved in organic solvent such as ethanol. Preferably, hydrogenated saturated hydrocarbon lecithin; triglyceride type hydrophilic organic compound such as caprylic/capric triglyceride; anionic surfactant such as diethylamine cetylphosphate, ascorbyl phosphate sodium, phosphotidylcholine or triethylamine coconyl glutamine sodium; or softening agent such as butylated hydroxy toluene may be further added to the organic solvent.

In the above step of preparing aqueous phase solution, the aqueous phase solution is prepared by dissolving hydrophilic active ingredient such as EGF in pure water. Preferably, anionic surfactant such as diethylamine cetylphosphate, ascorbyl phosphate sodium, phosphotidylcholine or triethylamine coconyl glutamine sodium; or chelating agent such as sodium salt of ethylenediaminetetraacetate may be further added to the aqueous phase solution.

The dissolution procedure of the esterified lecithin and physiologically active ingredient in solvent is preferably conducted at the temperature of 20° C. to 60° C. If the temperature is lower than 20° C., dissolution may be conducted, but the dissolution time is long, and there may be a stability problem after the dissolution. Here, if the temperature is higher than 60° C., coenzyme Q10 and/or EGF or the like as the physiologically active ingredient may be unstable.

After the oil-phase solution and aqueous phase solution as prepared above are mixed, the mixture is homogenized by using homomixer agitator. At this time, the liposome in the homogenized liposome solution exhibits a particle size of micrometer scale.

In the $3^{rd}$ step, nanoliposome solution is obtained by passing the homogeneously mixed solution of the $2^{nd}$ step through microfluidizer (M/F) under a pressure of 1000 psi or more, one or more times, and dispersing it to nanometer-sized liposome. If the pressure is lower than 1000 psi, it may be hard to form nanometer-sized liposome. Preferably, the homogeneously mixed solution is passed through microfluidizer (M/F) two or more times.

The liposome contained in the nanoliposome solution as prepared above forms a double liposome of aqueous phase/oil phase, in aqueous solution, and thus can also stabilize functional material of aqueous phase existing innermost, such as EGF and optional water-soluble anti-oxidant, and can further stabilize hydrophilic active ingredients such as EGF, and hydrophobic active ingredients such as coenzyme Q10 at the same time.

The present nanoliposome containing coenzyme Q10 and EGF with using esterified lecithin can be used in preparing a composition for skin such as cosmetics, medicaments for treating skin diseases, or the like by conventional methods.

The preferable amounts of raw materials used in preparing the composition are described in detail in the Examples. Also, the additives listed above may be substituted with other compatible ones, and the amounts of the additives may be adjusted properly according to the amount of functional material, to optimize the preparation conditions.

According to one embodiment, the present invention provides a composition for preventing or treating skin diseases, comprising nanoliposome which comprises a liposome membrane containing esterified lecithin, and epidermal growth factor included in inner space of the liposome membrane; and one or more natural extracts having anti-inflammatory activity.

The present composition uses epidermal growth factor in forms of inclusion in nanoliposome, by which the pharmaceutical stability of drug and the penetration into skin can be enhanced. Also, the esterified lecithin used in preparing liposome can provide additional moisturizing effect which is advantageous in treating skin diseases. Conventionally, skin diseases are caused from wound by burn, cut or the like, or radiation treatment to cancer patient. Thus, the esterified lecithin providing moisturizing effect to wounded region can exhibit better effect for treating skin diseases. Moreover, the esterified lecithin provides effects of softening skin and stimulating skin-penetration, thereby enhancing the penetration of epidermal growth factor and natural extract into skin. Further, since the present composition comprises nanoliposome prepared by containing esterified lecithin in liposome membrane, the conventional problems of heating and dispersing active ingredients at high temperature (70° C. or more), low stability, uniformity, or the like can be solved.

In the present composition, the epidermal growth factor may be used in a sufficient amount to treat skin diseases, and the effective amount for treatment may be varied depending on the patient's condition, age, gender, susceptibility or the like. The content of the epidermal growth factor in the present composition may be 1 to 50 wt %, based on total weight of the nanoliposome.

In the present composition, the nanoliposome including EGF may further comprise anti-oxidant. The anti-oxidant may comprise, but not limited to, coenzyme Q10, retinol, retinal, retinyl palmitate, retinoic acid, ascorbic acid, ascorbyl phosphate or salts thereof, or ascorbyl palmitate. Coenzyme Q10 plays a role of co-enzyme to promote energy generation of cell in human body, and has potent anti-oxidation power against active oxygen, and so its intake or application to skin is known to be effective for preventing the oxidation of cells, thereby maintaining skin elasticity and preventing the aging effectively. The amount of the anti-oxidant in the present composition may be 0.1 to 10 wt %, based on total weight of the nanoliposome.

The natural extract having anti-inflammatory activity comprises an extract from natural products which is known as containing anti-inflammatory ingredient, without limitation. The natural extract having anti-inflammatory activity useful for the present composition may comprise an extract from one or more natural products such as *Camellia japonica, Viscum album* L. var. *coloratum, Ulmi cortex, Lillium brownii* F.E., *Pimellia ternata Thunb Breit, Bletilla striata Reichb.* fil., *Paeonia lactiflora* Pall, *Boswellia carterii* Birdw, *Anemarrhena rhizome, Aralia cortex*, Rehmaniae radix, Dioscoreae Radix, Comi Fructus, Hoelen, Moutan Cortex Radicis, Schizandrae Fructus, Asparagi Tuber, Liriopsis Tuber, Fritillariae Bulbus, Armeniacae Semen, Pinelliae Tuber, Platicodi Radix, Scutellariae Radix, Coptidis Rhizoma, or the like. The natural extract may be used alone or in combination with two or more extracts. Preferably, the natural extract is from *Camellia japonica* and/or *Viscum album* L. var. *coloratum*, and more preferably, an extract from *Camellia japonica* as disclosed in Korean Laid-open Publication No. 10-2005-0058635 or an extract from *Viscum album* L. var. *coloratum* as disclosed in Korean Laid-open Publication No. 10-2006-0025423.

The natural extract may be used in various amounts depending on natural products used, extraction method, or the like. Conventionally, the content of the natural extract in the present composition may be 0.01 to 10 wt %, based on total weight of the composition.

The present composition for preventing or treating skin diseases may be prepared by formulating the nanoliposome which is prepared as described above to comprise a liposome membrane containing esterified lecithin, and epidermal growth factor included in inner space of the liposome membrane, with the natural extract having anti-inflammatory activity. The formulation may be conducted by dispersing and/or dissolving the natural extract having anti-inflammatory activity in the nanoliposome solution as obtained above. The dispersion and/or dissolution are preferably conducted at room temperature.

If necessary, the present composition may further comprise a stabilizing agent such as amino acid, sodium bisulfite, sodium metabisulfite, sodium sulfite, ethylendiaminetetraacetate disodium, sodium bisulfide, sodium formaldehyde sulfoxylate, thiourea, acetone sodium bisulfite or the like; a moisturizing agent such as ceramide, glycerin, propylene glycol, ammonium alginate, cyclomethicone, dimethicone, polydextrose, sodium hyaluronate, sodium lactate, solbitol, triacetin, triethanolamine, xylitol or the like; an emulsifying agent such as polyoxyethylene alkylether, polyoxyethylene castor oil derivative, polyoxyethylene sorbitan fatty acid ester, polyoxyethylene stearate or the like; or a pharmaceutically acceptable additive such as sodium benzoate, methyl paraoxybenzoate, ethyl paraoxybenzoate, (iso)propyl paraoxybenzoate, (iso)butyl paraoxybenzoate, sorbic acid, potassium sorbate, sodium sorbate, dehydroacetic acid, sodium dehydroacetate, benzalkonium chloride, benzentonium chloride, phenol, cresol, chlorocresol, benzyl alcohol or the like. The present composition may be formulated to a medicine for external use such as ointment, cream, lotion, etc.

Also, the present composition may be prepared in various forms of cosmetics such as skin lotion, nutritional lotion, nutritional cream, massage cream, nutritional essence, pack, make-up base, foundation, body oil, hair oil, shampoo, rinse, etc.

The present invention will be more specifically explained by the following examples.

However, it should be understood that the following examples are intended to illustrate the present invention, and cannot limit the scope of the present invention in any manner.

EXAMPLES

Synthesis of Esterified Lecithin

Example 1

With heating 200 g of tetrahydrofuran solvent to a temperature of 70° C., 31 g of hydrogenated saturated hydrocarbon lecithin was added thereto and dissolved. After dissolving the lecithin clearly, 3 g of anhydrous malic acid was added to the mixture and dissolved. After dissolving the anhydrous malic acid clearly, 0.5 g of triethylamine as catalyst was added thereto, and the reaction was maintained under reflux for more than 3 hours. After completing the reaction, the resultant mixture was dried under vacuum at 45° C. to obtain esterified lecithin in white powder form.

Example 2

An esterified lecithin was synthesized by the same method as Example 1, except for using 2.5 g of anhydrous acetic acid instead of the anhydrous malic acid.

Preparation of Nanoliposome Solution

Example 3

1) Preparation of Oil-Phase Solution 15 g of esterified lecithin, 15 g of hydrogenated saturated hydrocarbon lecithin, 200 g of caprylic/capric triglyceride (MCT), 10 g of diethylamine cetylphosphate, and 0.5 g of butylated hydroxy toluene (BHT) were added to 110 g of ethanol, and the mixture was heated to about 40° C., stirred and dissolved. The dissolved mixture was then cooled to room temperature to obtain oil-phase solution.

2) Preparation of Aqueous Phase Solution 0.5 g of Na-EDTA, 1 g of ascorbyl phosphate sodium (NAP), and 2 g of EGF were dissolved in 650 g of water under stirring at room temperature to obtain aqueous phase solution.

3) Mixing of the Oil-Phase Solution and the Aqueous Phase Solution

The aqueous phase solution as obtained above was added to the prepared oil-phase solution, and the mixture was sufficiently agitated with using homomixer for more than 5 minutes to obtain homogeneous mixture.

4) Preparation of Nanoliposome

Nanoliposome solution was prepared by passing the obtained homogeneous mixture through microfluidizer under the pressure of more than 1000 psi one or more times to disperse the liposome in nanometer size. The temperature condition of the passing procedure was cooled to below room temperature by using cooling water.

Example 3'

A nanoliposome solution was prepared by the same method as Example 3, except for using 2.4 g of EGF.

Example 4

A nanoliposome solution was prepared by the same method as Example 3, except for using 30 g of esterified lecithin.

Example 5

A nanoliposome solution was prepared by the same method as Example 3, except for using 10 g of lauryl betaine (betaine type amphiphilic surfactant) instead of diethylamine cetylphosphate (anionic surfactant).

Example 6

A nanoliposome solution was prepared by the same method as Example 3, except for using 50 g of esterified lecithin, and not using hydrogenated saturated hydrocarbon lecithin nor diethylamine cetylphosphate.

Example 7

1) Preparation of Oil-Phase Solution 15 g of esterified lecithin, 15 g of hydrogenated saturated hydrocarbon lecithin, 200 g of caprylic/capric triglyceride (MCT), 10 g of diethylamine cetylphosphate, 0.5 g of butylated hydroxy toluene (BHT) and 10 g of coenzyme Q10 were added to 110 g of ethanol, and the mixture was heated to about 40° C., stirred and dissolved. The dissolved mixture was then cooled to room temperature to obtain oil-phase solution.

2) Preparation of Nanoliposome

According to the same method as Example 3, an aqueous phase solution was prepared, thus prepared aqueous phase solution was mixed with the oil-phase solution as prepared above, and the mixture was dispersed in nanometer size to prepare nanoliposome solution.

Example 8

A nanoliposome solution was prepared by the same method as Example 7, except for using 30 g of esterified lecithin, and not using hydrogenated saturated hydrocarbon lecithin.

Example 9

A nanoliposome solution was prepared by the same method as Example 7, except for using 10 g of lauryl betaine (betaine type amphiphilic surfactant) instead of diethylamine cetylphosphate.

Example 10

A nanoliposome solution was prepared by the same method as Example 7, except for using 50 g of esterified lecithin, and not using hydrogenated saturated hydrocarbon lecithin nor diethylamine cetylphosphate.

Example 11

1) 15 g of esterified lecithin, 15 g of hydrogenated saturated hydrocarbon lecithin, 200 g of caprylic/capric triglyceride (MCT), 0.5 g of butylated hydroxy toluene (BHT) and 10 g of coenzyme Q10 were added to 110 g of ethanol, and the mixture was heated to about 50° C., stirred and dissolved. The dissolved mixture was then cooled to room temperature.

2) 2.4 g of EGF was dissolved in 10 g of distilled water. Thus obtained solution was added to the solution prepared in the above step 1).

3) The mixture solution prepared in the above step 2) was sufficiently agitated with using homomixer for more than 10 minutes.

4) The solution prepared in the above step 3) was passed through microfluidizer under the pressure of more than 1000 psi.

5) The solution prepared in the above step 4) was added to 650 g of water containing 0.5 g of Na-EDTA and 1 g of ascorbyl phosphate sodium with agitation by homomixer.

6) After the addition, the mixture was agitated sufficiently for more than 10 minutes.

7) The solution prepared in the above step 6) was passed through microfluidizer one or more times to obtain a double-layered nanoliposome solution.

Example 12

A nanoliposome solution was prepared by the same method as Example 11, except for using 35 g of esterified lecithin, and not using hydrogenated saturated hydrocarbon lecithin.

Example 13

A nanoliposome solution was prepared by the same method as Example 11, except for using 50 g of esterified lecithin, and not using hydrogenated saturated hydrocarbon lecithin.

Example 14

1) 1 g of diethylamine cetylphosphate, 200 g of caprylic/capric triglyceride (MCT), 10 g of esterified lecithin, 0.5 g of butylated hydroxy toluene and 10 g of coenzyme Q10 were added to 110 g of ethanol, and the mixture was stirred vigorously and dissolved at room temperature to obtain oil-phase solution.

2) 2.3 g of EGF was dissolved in 10 g of distilled water. Thus obtained solution was added to the solution prepared in the above step 1).

3) The mixture solution prepared in the above step 2) was sufficiently agitated with using homomixer for more than 10 minutes.

4) The solution prepared in the above step 3) was passed through microfluidizer under the pressure of more than 1000 psi.

5) The solution prepared in the above step 4) was added to 650 g of water containing 0.5 g of Na-EDTA and 1 g of ascorbyl phosphate sodium with agitation by homomixer.

6) After the addition, the mixture was agitated sufficiently for more than 10 minutes.

7) The solution prepared in the above step 6) was passed through microfluidizer one or more times to obtain a double-layered nanoliposome solution.

Example 15

A nanoliposome solution was prepared by the same method as Example 14, except for using 1 g of ascorbyl phosphate sodium instead of diethylamine cetylphosphate.

Example 16

A nanoliposome solution was prepared by the same method as Example 14, except for using 1 g of triethylamine coconyl glutamine sodium (MIAMI CT130, anionic surfactant) instead of diethylamine cetylphosphate.

Example 17

A nanoliposome solution was prepared by the same method as Example 14, except for using 1 g of laurylamine propyl betaine (betaine type amphiphilic surfactant) instead of diethylamine cetylphosphate.

Comparative Example

A nanoliposome solution was prepared by the same method as Example 7, except for using 30 g of hydrogenated saturated hydrocarbon lecithin, and not using esterified lecithin.

Preparation of Formulation for External Use

Example 18

5 ml of the nanoliposome solution prepared in Example 3 was added to 95 g of nutritional lotion base containing Camellia japonica extract which was prepared according to the example 2 of Korean Laid-open Publication No. 10-2005-0058635. Then, the mixture was stirred at room temperature for 20 minutes to obtain a composition for preventing or treating skin diseases.

Example 19

5 ml of the nanoliposome solution prepared in Example 3 was added to 95 g of nutritional lotion base containing *Viscum album* L. var. *coloratum* extract which was prepared according to the formulation example 1 of Korean Laid-open Publication No. 10-2006-0025423. Then, the mixture was stirred at room temperature for 20 minutes to obtain a composition for preventing or treating skin diseases.

Test Example 1

Stability Test

For the nanoliposome solutions prepared in the above Example 8 (using esterified lecithin only), Example 7 (using esterified lecithin and hydrogenated saturated hydrocarbon lecithin) and Comparative Example (using hydrogenated saturated hydrocarbon lecithin only), the average particle size and gelation due to long-term storage at room temperature were compared. The results are shown in the following Table 1. Also, observation was conducted to confirm occurrence of the Ostwald ripening, which is a mechanism of particle growth by depositing substances on bigger particles due to particle size difference between particles in solution [Ostwald, Z Phys. Chem. (34), 1900, 495-5031].

If a liposome solution is stored for a long time, gelation caused by coagulation occurs generally. Thus, the time to gelate was determined by the time for which the gelated solution was not re-dispersed nor re-dissolved in spite of re-stirring.

TABLE 1

Results of the Stability Test

| Solution sample | Average particle size of liposome | Time to gelate | Remarks |
|---|---|---|---|
| Example 8 | 470 nm | 25 days | The gelation proceeded slowly. |
| Example 7 | 750 nm | 20 days | With the gelation, the Ostwald ripening proceeded in part. |
| Comparative Example | 1500 nm | 15 days | The gelation and Ostwald ripening occurred simultaneously, and the liposome was separated from solvent. |

* Test temperature: room temperature (20° C. in average)

<Absorbance and Transmittance of Nanoliposome Solution in UV/Visible Region>

For the nanoliposome solution having double-layered membrane of EGF (aqueous phase)/coenzyme Q10 (oil phase) in the above Example 8 prepared by using the esterified lecithin only according to the present invention, the absorbance and transmittance in UV/Visible region were determined. The results are shown in FIGS. 1 and 2.

Figure 2:
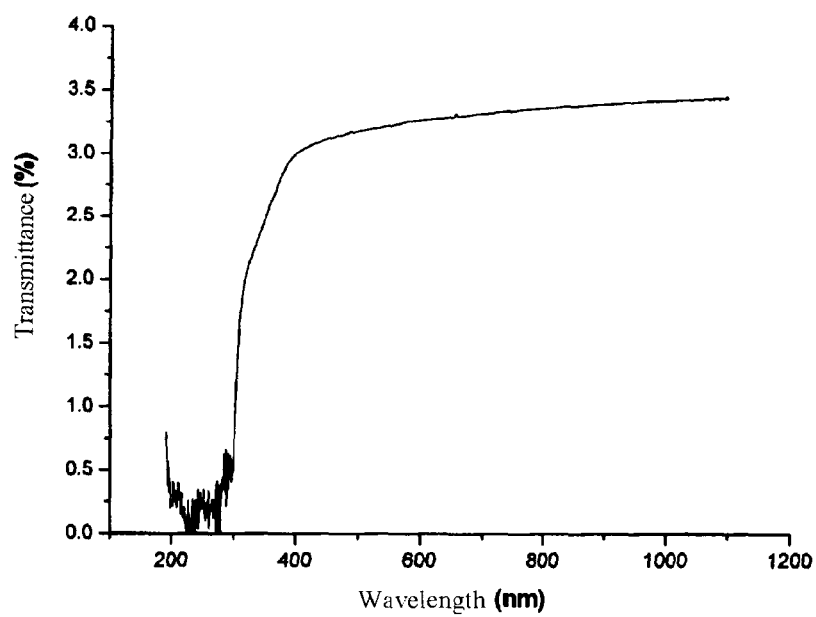
FIG. 2 is a graph representing UV/Visible transmittance (%) of the solution of nanoliposome having double layered membrane of EGF/coenzyme Q10, which is prepared by using esterified lecithin according to the present invention.

As shown in FIGS. 1 and 2, the visible light in 400 nm to 700 nm region was not scattered nor absorbed substantially, which means that the prepared nanoliposome solution was very clear, and the size of liposome was uniform.

<Measurement of Particle Size Distribution>

For the nanoliposome solution having double-layered membrane prepared in the above Example 8, the particle size distribution was measured. The result is shown in FIG. 3.

Figure 3:
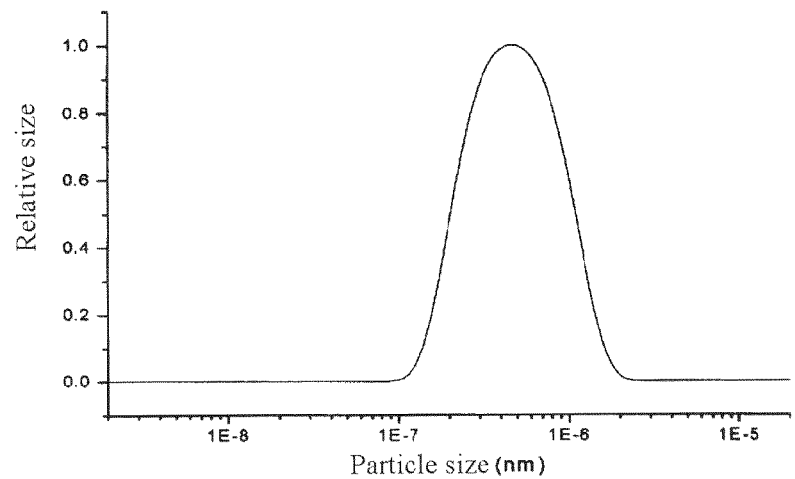
FIG. 3 is a graph representing particle size distribution of nanoliposome having double layered membrane of EGF/coenzyme Q10, which is prepared by using esterified lecithin according to the present invention.

As shown in FIG. 3, the nanoliposome particles were distributed within a narrow range, which means that the prepared nanoliposome solution was very clear, and the size of liposome was uniform.

Test Example 2

To compare the stability of EGF when it was nanoliposomized and the nanoliposome was dispersed in cosmetics, a phosphate buffer solution of 10 mM EGF with pH 7.4, the EGF nanoliposome solution of Example 3 and the composition of EGF nanoliposome dispersion of Example 18 were stored under a severe condition of 40° C. and 75% RH for three months, and the relative stabilities were compared. The residual amounts were analyzed with using ELISA method. The results are shown in the following Table 2. As shown in Table 2, the stability of EGF included in nanoliposome increased significantly, compared with the buffer solution, and the stability of EGF in the formulated composition further increased.

TABLE 2

Results of the Stability Test - Comparison of the Stabilities of EGF in phosphate buffer solution of 10 mM EGF with pH 7.4, EGF nanoliposome, and Composition of EGF nanoliposome dispersion (n = 3)

| | EGF content (%) | | |
|---|---|---|---|
| Time | phosphate buffer solution with pH 7.4 | EGF nanoliposome solution | composition containing EGF nanoliposome |
| 2 weeks | 72.23 ± 2.3 | 95.42 ± 3.0 | 96.51 ± 1.0 |
| 4 weeks | 55.82 ± 5.5 | 88.57 ± 2.8 | 89.95 ± 7.2 |
| 8 weeks | 31.67 ± 4.7 | 67.04 ± 4.1 | 75.36 ± 2.2 |
| 12 weeks | 23.39 ± 1.2 | 51.08 ± 4.2 | 64.18 ± 1.6 |

Test Example 3

Figure 4:
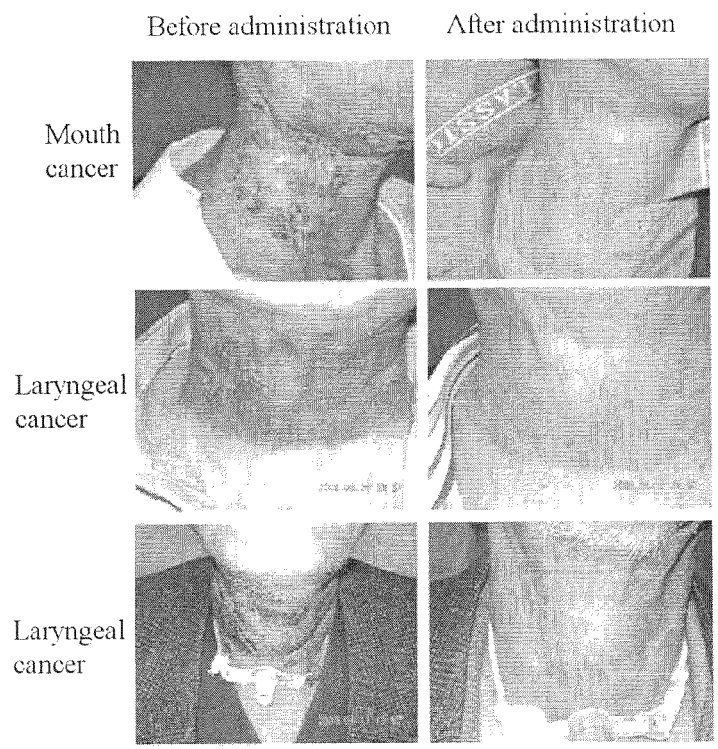
FIG. 4 is to show the treatment effect of the present composition when the composition comprising nanoliposome is administered to a patient of mouth cancer, and a patient of laryngeal cancer, who have dermatitis caused by radiation treatment.

For a mouth cancer patient who had been subjected to 33 times of radiation treatments (59.4Gy) and thus had a severe inflammation on the skin after the radiation treatments (the left column of FIG. 4), the composition prepared in Example 18 was applied to cover the diseased part thoroughly, 2 times per day for about 1.5 months (2006 Feb. 28~2006 Apr. 17). During the administration period of the composition, the diseased part had been observed everyday. After 5 days from the administration, the inflammation in the diseased part became alleviated significantly. After 10 days, the skin color of the diseased part became changed, and after about 1 month, the diseased part was recovered to nearly normal skin (FIG. 4).

For two laryngeal cancer patients who had a severe inflammation on the skin, the composition prepared in Example 18 was applied to cover the diseased part thoroughly, 2 times per day for about 1 month (2006 Mar. 29~2006 Apr. 17) and for about 1 week (2006 Apr. 11~2006 Apr. 18). During the administration period, the diseased part had been observed everyday. After about 1 month and about 1 week, respectively, the diseased part was recovered to nearly normal skin (FIG. 4).

INDUSTRIAL APPLICABILITY

The nanoliposome according to the present invention forms a liposome membrane containing esterified lecithin, and so can liposomize thermally unstable functional materials safely at low temperature and capture both the hydrophilic materials and hydrophobic materials simultaneously. Also, since anhydrous organic acid for removing keratinous substance is used as functional group, it is advantageous to exhibit various functional effects such as removing keratinous substance or skin-softening.

Also, the present composition for preventing or treating skin diseases comprises epidermal growth factor included in the nanoliposome, thereby showing an excellent effect of stimulating skin-penetration and good pharmaceutical stability. Moreover, the esterified lecithin used in preparing liposome can provide additional moisturizing effect which is advantageous in treating skin diseases. Conventionally, skin diseases are caused from wound by burn, cut or the like, or radiation treatment to cancer patient. Thus, the esterified lecithin providing moisturizing effect to wounded region can exhibit better effect for treating skin diseases. Further, the esterified lecithin provides effects of softening skin and stimulating skin-penetration, thereby enhancing the penetration of epidermal growth factor and natural extract into skin. Furthermore, since the present composition comprises nanoliposome prepared by containing esterified lecithin in liposome membrane, the conventional problems of heating and dispersing active ingredients at high temperature (70° C. or more), low stability and uniformity, or the like can be solved.

The invention claimed is:

1. A nanoliposome comprising a liposome membrane containing lecithin wherein at least 50% of the lecithin is esterified lecithin, and one or more physiologically active ingredients included in inner space of the liposome membrane, wherein the esterified lecithin is a reaction product of hydrogenated lecithin and an organic acid, selected from the group consisting of anhydrous acetic acid, anhydrous malic acid, anhydrous lactic acid, anhydrous glycolic acid, anhydrous citric acid and anhydrous oxalic acid, wherein the lecithin is phosphatidylcholine.

2. The nanoliposome according to claim 1, wherein the physiologically active ingredient is one or more selected from the group consisting of coenzyme Q10 and epidermal growth factor.

3. The nanoliposome according to claim 1, further comprising one or more compounds selected from the group consisting of hydrogenated lecithin, anionic surfactant, triglyceride type organic compound, softening agent, chelating agent and betaine type amphiphilic surfactant.

4. A method for preparing a nanoliposome comprising a liposome membrane containing lecithin wherein at least 50% of the lecithin is esterified lecithin comprising:
the $1^{st}$ step of preparing esterified lecithin by reacting hydrogenated lecithin with an organic acid, selected from the group consisting of anhydrous acetic acid, anhydrous malic acid, anhydrous lactic acid, anhydrous glycolic acid, anhydrous citric acid and anhydrous oxalic acid, wherein the lecithin is phosphatidylcholine;
the $2^{nd}$ step of dissolving the esterified lecithin and one or more physiologically active ingredients in a solvent; and
the $3^{rd}$ step of dispersing the resultant solution to obtain liposome in nanometer size.

5. The method according to claim 4, wherein the physiologically active ingredient is one or more selected from the group consisting of coenzyme Q10 and epidermal growth factor.

6. The method according to claim 5, wherein the $2^{nd}$ step comprises the steps of:
preparing oil-phase solution by dissolving esterified lecithin and coenzyme Q10 into organic solvent;
preparing aqueous phase solution by dissolving epidermal growth factor in aqueous solvent; and
mixing the oil-phase solution and the aqueous phase solution.

7. The method according to claim 4, wherein the $2^{nd}$ step is conducted at the temperature of 20° C. to 60° C.

8. A composition for preventing or treating skin diseases, comprising a nanoliposome which comprises a liposome membrane containing lecithin wherein at least 50% of the lecithin is esterified lecithin, and epidermal growth factor included in inner space of the liposome membrane; and one or more natural extracts having anti-inflammatory activity, wherein the esterified lecithin is a reaction product of hydrogenated lecithin and an organic acid, selected from the group consisting of anhydrous acetic acid, anhydrous malic acid, anhydrous lactic acid, anhydrous glycolic acid, anhydrous citric acid and anhydrous oxalic acid, wherein the lecithin is phosphatidylcholine.

9. The composition according to claim 8, wherein the nanoliposome further includes one or more anti-oxidants selected from the group consisting of coenzyme Q10, retinol, retinal, retinyl palmitate, retinoic acid, ascorbic acid, ascorbyl phosphate or salts thereof, and ascorbyl palmitate.

10. The composition according to claim 8, wherein the natural extract is an extract from one or more natural products selected from the group consisting of *Camellia japonica, Viscum album* L. var. *coloratum, Ulmi cortex, Lillium brownii* F.E., *Pimellia ternata* Thunb Breit, *Bletilla striata* Reichb. fil., *Paeonia lactiflora* Pall, *Boswellia carterii* Birdw, *Anemarrhena rhizome, Aralia cortex*, Rehmaniae radix, Dioscoreae Radix, Corni Fructus, Hoelen, Moutan Cortex Radicis, Schizandrae Fructus, Asparagi Tuber, Liriopsis Tuber, Fritillariae Bulbus, Armeniacae Semen, Pinelliae Tuber, Platicodi Radix, Scutellariae Radix, and Coptidis Rhizoma.

11. The composition according to claim 8, wherein the natural extract is an extract from *Camellia japonica* or *Viscum album* L. var. *coloratum*.

12. The composition according to claim 8, wherein the liposome membrane comprises hydrogenated lecithin, ceramide, or mixtures thereof, in addition to the esterified lecithin.

13. The composition according to claim 8, wherein the nanoliposome further comprises one or more selected from the group consisting of anionic surfactant, triglyceride type organic compound, softening agent, chelating agent and amphiphilic surfactant.

* * * * *